United States Patent
Neumann

(10) Patent No.: US 12,280,547 B2
(45) Date of Patent: Apr. 22, 2025

(54) METHODS AND SYSTEMS FOR ADDITIVE MANUFACTURING OF NUTRITIONAL SUPPLEMENT SERVINGS

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 0 days.

(21) Appl. No.: 16/911,994

(22) Filed: Jun. 25, 2020

(65) Prior Publication Data

US 2021/0402707 A1 Dec. 30, 2021

(51) Int. Cl.
*B29C 64/393* (2017.01)
*A23L 33/00* (2016.01)
(Continued)

(52) U.S. Cl.
CPC ............ *B29C 64/393* (2017.08); *A23L 33/40* (2016.08); *A23P 30/10* (2016.08); *B29C 64/153* (2017.08);
(Continued)

(58) Field of Classification Search
CPC ... B29C 64/393; B29C 64/153; B29C 64/268; B33Y 10/00; B33Y 30/00; B33Y 50/02;
(Continued)

(56) References Cited

U.S. PATENT DOCUMENTS

| | | | |
|---|---|---|---|
| 6,510,430 B1 * | 1/2003 | Oberwager | G06F 19/3418 |
| | | | 128/921 |
| 7,762,181 B2 | 7/2010 | Boland et al. | |

(Continued)

FOREIGN PATENT DOCUMENTS

WO   WO-2014193226 A1 *  12/2014  ............. A21D 13/80

OTHER PUBLICATIONS https://www.eurekalert.org/pub_releases/2018-04/eb2-3pf041318.php.
https://khni.kerry.com/news/blog/is-3d-printing-the-future-of-personalized-nutrition/#:~:text=One%20example%20of%20the%20positive,ink%20in%20a%20predetermined%20way.
https://www.foodingredientsfirst.com/news/3d-printed-food-a-new-frontier-in-personalized-nutrition.html.

*Primary Examiner* — Steven N Leff
(74) *Attorney, Agent, or Firm* — Caldwell Intellectual Property Law

(57) ABSTRACT

A system for additive manufacturing of nutritional supplement servings includes a computing device configured to receive nutritional needs of a user, determine a nutritional input to the user, detect at least a nutrition deficiency as a function of the plurality of nutritional needs and the nutritional input, calculate at least a supplement dose from the plurality of nutritional needs and at the least a nutrition deficiency, select an ingredient combination as a function of the at least a supplement dose, wherein selecting further includes receiving a plurality of ingredients stored at an additive manufacturing device, wherein the plurality ingredients includes a plurality of supplement ingredients and at least a substrate ingredient and selecting an ingredient combination including at least a substrate ingredient and at least a supplement ingredient as a function of the nutritional deficiency, and initiating manufacture of a nutritional supplement serving at the additive manufacturing device.

16 Claims, 6 Drawing Sheets

(51) Int. Cl.
*A23P 30/10* (2016.01)
*B29C 64/153* (2017.01)
*B29C 64/268* (2017.01)
*B33Y 10/00* (2015.01)
*B33Y 30/00* (2015.01)
*B33Y 50/02* (2015.01)
*G05B 13/02* (2006.01)

(52) U.S. Cl.
CPC ............ *B29C 64/268* (2017.08); *B33Y 10/00* (2014.12); *B33Y 30/00* (2014.12); *B33Y 50/02* (2014.12); *G05B 13/0265* (2013.01); *A23V 2002/00* (2013.01)

(58) Field of Classification Search
CPC ..... A23P 30/10; A23L 33/40; G05B 13/0265; G06G 30/0621; G06G 30/0631
See application file for complete search history.

(56) References Cited

U.S. PATENT DOCUMENTS

| | | | |
|---|---|---|---|
| 10,332,418 | B2 | 6/2019 | Hardee et al. |
| 10,537,129 | B2 | 1/2020 | Corthesy-Malnoe et al. |
| 2002/0004749 | A1* | 1/2002 | Froseth .............. G06Q 30/0603 |
| | | | 705/16 |
| 2011/0054928 | A1* | 3/2011 | Sullivan ................. G16H 20/60 |
| | | | 705/2 |
| 2013/0034633 | A1 | 2/2013 | von Hasseln |
| 2014/0322678 | A1* | 10/2014 | Briancon .............. G06F 16/284 |
| | | | 434/127 |
| 2016/0106142 | A1 | 4/2016 | Contractor et al. |
| 2017/0156386 | A1 | 6/2017 | Baetge et al. |
| 2018/0116272 | A1 | 5/2018 | Hardee et al. |
| 2019/0142020 | A1 | 5/2019 | Contractor et al. |

* cited by examiner

METHODS AND SYSTEMS FOR ADDITIVE MANUFACTURING OF NUTRITIONAL SUPPLEMENT SERVINGS

FIELD OF THE INVENTION

The present invention generally relates to the field of additive manufacturing. In particular, the present invention is directed to methods and systems for additive manufacturing of nutritional supplement servings.

BACKGROUND

Design of systems for analysis of nutritional data is often frustrated by the extreme complexity and variability of the subject matter between subjects. A vast multiplicity of factors to be considered is further complicated by a complex array of subtle, but crucial data. Worse still, a given factor may vary significantly between subjects, and in ways that can frustrate consistent application of nutritional data to analytical techniques.

SUMMARY OF THE DISCLOSURE

In an aspect, a system for additive manufacturing of nutritional supplement servings includes a computing device designed and configured to receive a plurality of nutritional needs of a user, determine a nutritional input to the user, detect at least a nutrition deficiency as a function of the plurality of nutritional needs and the nutritional input, calculate at least a supplement dose from the plurality of nutritional needs and at the least a nutrition deficiency, select an ingredient combination as a function of the at least a supplement dose, wherein selecting further includes receiving a plurality of ingredients stored at an additive manufacturing device, wherein the plurality ingredients includes a plurality of supplement ingredients and at least a substrate ingredient and selecting an ingredient combination including at least a substrate ingredient and at least a supplement ingredient as a function of the nutritional deficiency, and initiating manufacture of a nutritional supplement serving at the additive manufacturing device.

In another aspect, a method of additive manufacturing of nutritional supplement servings includes receiving, at a computing device, a plurality of nutritional needs of a user, determining, by the computing device, a nutritional input to the user, detecting, by the computing device, at least a nutrition deficiency as a function of the plurality of nutritional needs and the nutritional input, calculating, by the computing device, at least a supplement dose from the plurality of nutritional needs and at the least a nutrition deficiency, selecting, by the computing device, an ingredient combination as a function of the at least a supplement dose, wherein selecting further includes receiving a plurality of ingredients stored at an additive manufacturing device, wherein the plurality ingredients includes a plurality of supplement ingredients and at least a substrate ingredient and selecting an ingredient combination including at least a substrate ingredient and at least a supplement ingredient as a function of the nutritional deficiency and initiating, by the computing device, manufacture of a nutritional supplement serving at, the additive manufacturing device.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to a system and method for additively manufacturing nutritional supplement servings; after determining supplement dose 132s to be administered. A machine learning process may calculate a nutritional deficiency 120 based on a nutritional input 116 and a nutritional need. A machine learning process may determine an appropriate supplement plan based on at least a nutritional deficiency 120. Supplement plan may include supplement regimen, including in non-limiting examples supplement dosage, frequency of use, and how supplement address deficiency. Supplement serving may be additively manufactured as a function of supplement plan.

Figure 1:
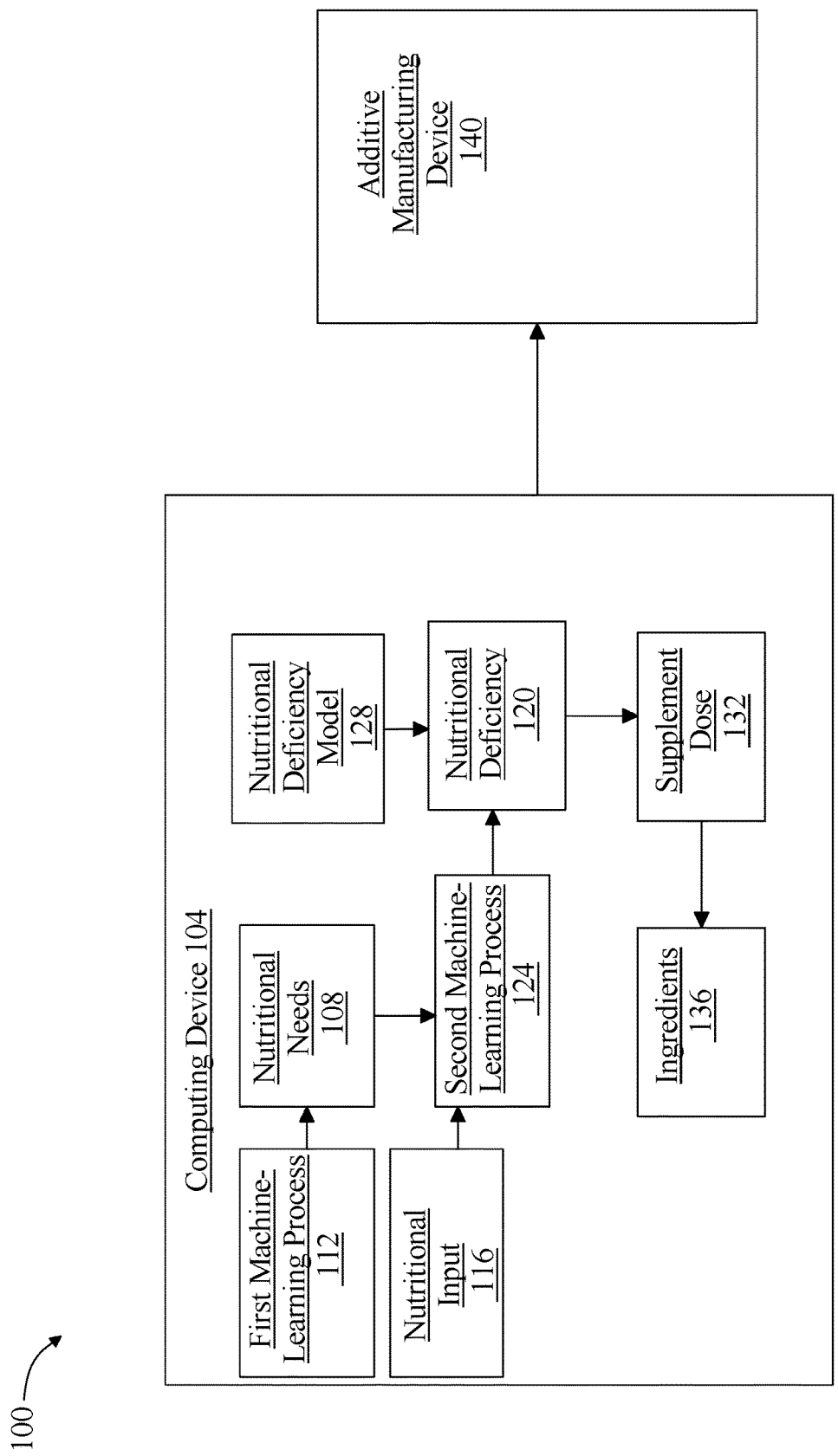
FIG. 1 is a block diagram of an exemplary embodiment of a system for additive manufacturing of nutritional supplement servings.

Referring now to FIG. 1, an exemplary embodiment of a system 100 for additive manufacturing of nutritional supplement servings is illustrated. System 100 includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently, or may include two or more computing device 104 operating in concert, in parallel, sequentially or the like; two or more computing device may be included together in a single computing device 104 or in two or more computing device. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing device, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing device in a first location and a second computing device 104 or cluster of computing device in a second location. Computing device 104 may include one or more computing device dedicated to data storage, security, distribution of traffic for load balancing, and the like. Computing device 104 may distribute one or more computing tasks as described below across a plurality of computing device of computing device 104, which may operate in parallel, in series, redundantly, or in any other manner used for distribution of tasks or memory between computing device. Computing device 104 may be implemented using a "shared nothing" architecture in which data is cached at the worker, in an embodiment, this may enable scalability of system 100 and/or computing device 104.

Computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 is configured to receive a plurality of nutritional needs 108 of a user. As used in this disclosure, a "nutritional need," is a quantity of at least a nutrient and/or of a plurality of nutrients that is recommended for health of user. Nutrient may refer to, without limitation, macronutrients, such as protein, including non-essential amino acids, essential amino acids, fats including non-essential fats, essential fats such as long-chain polyunsaturated fatty acids (LC-PUFAs), short-chain polyunsaturated fatty acids (SC-PUFAs), omega fatty acids, carbohydrates, including digestible and non-digestible carbohydrates such as dietary fiber, inulin, psyllium, and methylcellulose; micronutrients, such as vitamin A, thiamin (vitamin B1), riboflavin (vitamin B2), niacin (vitamin B3), pantothenic acid (vitamin B5), vitamin B6, biotin (vitamin B7), folate (vitamin B12), vitamin C, vitamin D2, vitamin D3, vitamin E, vitamin K1, vitamin K2; minerals such as calcium, phosphorous, potassium, sodium, magnesium; trace elements such as iron, sulfur, manganese, selenium, chromium, molybdenum, copper, cobalt; halides such a chloride and iodine; electrolytes and salts including bicarbonate, creatine, and phosphocreatine; caloric content, or any other substance that provides nourishment essential for growth and maintenance of a user.

Computing device 104 may be designed and configured to receive plurality of nutritional needs 108 by receiving plurality from another device. Alternatively or additionally, computing device 104 may receive plurality of nutritional needs by receiving at least a biological extraction and generate plurality of nutritional needs 108 as a function of at least a biological extraction. A "biological extraction," as used in this disclosure may refer to any biomarker, genetic or epigenetic indication, microbiome, or any chemical, biological, or physiological markers of data of a user, including for instance, and without limitation, as described in U.S. Nonprovisional application Ser. No. 16/865,740, filed on May 4, 2020, and entitled "METHODS AND SYSTEMS FOR SYSTEM FOR NUTRITIONAL RECOMMENDATION USING ARTIFICIAL INTELLIGENCE ANALYSIS FOR IMMUNE IMPACTS," the entirety of which is incorporated herein by reference.

Figure 2:
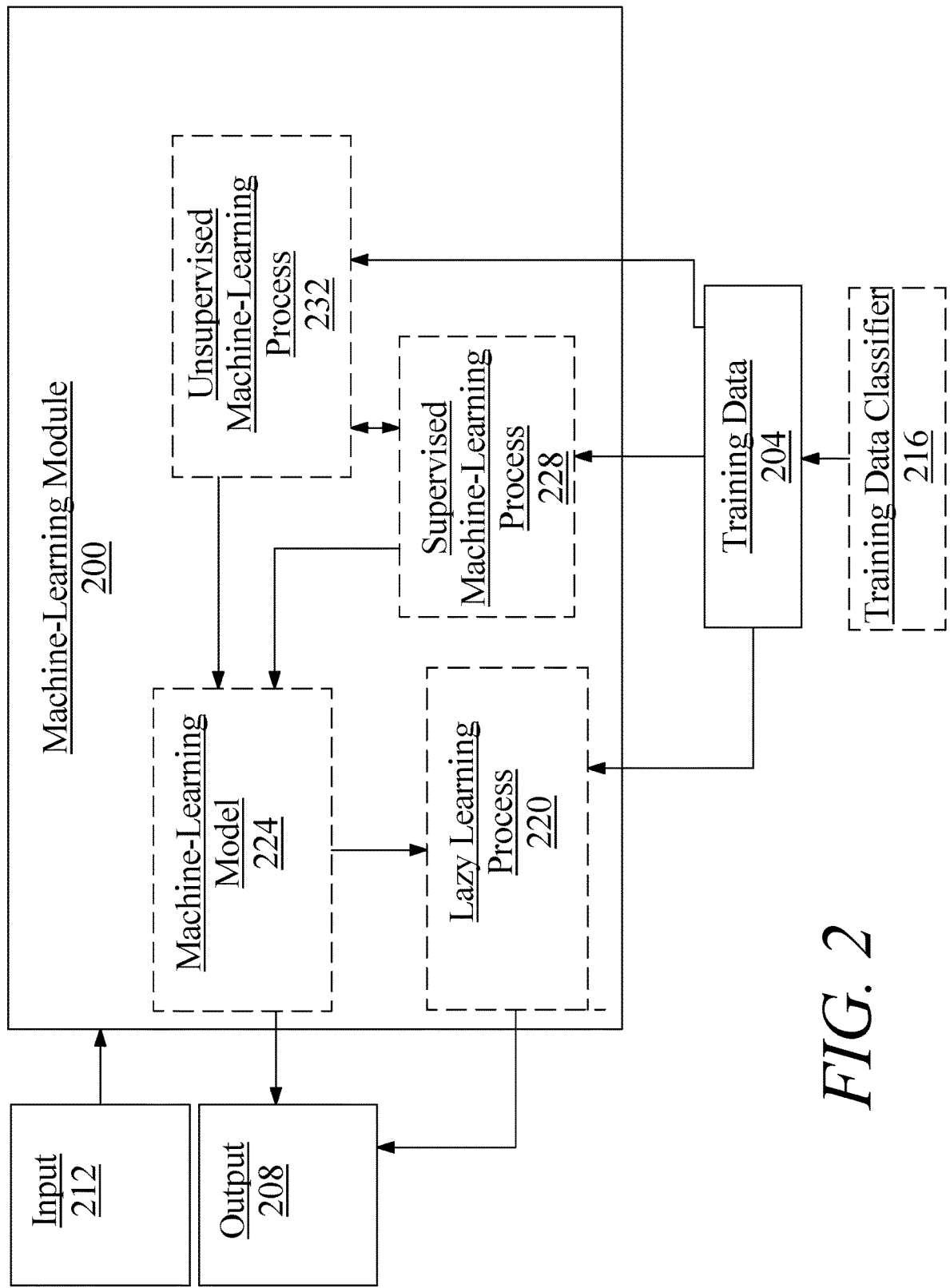
FIG. 2 is a block diagram of an exemplary embodiment of a machine-learning module.

Referring now to FIG. 2, an exemplary embodiment of a machine-learning module 200 that may perform one or more machine-learning processes as described in this disclosure is illustrated. Machine-learning module may include any suitable Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm that will be performed by a computing device 104/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 200 may generate a classifier using a classification algorithm, defined as a processes whereby a computing device 104 and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Continuing in reference to FIG. 2, a classifier 216 may indicate a subset of users mutually similar in at least one or more elements of data including biological extraction data, user-reported data, nutritional needs 108, nutritional input 116s, nutritional deficiencies, supplement plan, and/or any other available data, to match a user to a nutritional standard. Matching a user to a nutritional standard via a classifier 216 or subset of users may correspond to identifying any mathematical, correlational, proportional, and/or any other relationship between a user's biological extraction, nutritional needs 108, nutritional input 116s, nutritional deficiencies, and/or supplement plan, and other users. A classifier 216 may be an input to a machine learning process to calculate, modify, or otherwise generate nutritional needs 108, nutritional input 116s, nutritional deficiencies, and/or supplement plan information for a user. Classifier 216s generated from a classification algorithm may be stored and/or retrieved in a database, such as a nutritional database, for use by machine learning process, as described herein, including for instance, and without limitation, as described in U.S. Nonprovisional application Ser. No. 16/865,740, filed on May 4, 2020, and entitled "METHODS AND SYSTEMS FOR SYSTEM FOR NUTRITIONAL RECOMMENDATION USING ARTIFICIAL INTELLIGENCE ANALYSIS FOR IMMUNE IMPACTS," the entirety of which is incorporated herein by reference.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning model 224s. A "machine-learning model 224," as used in this disclosure, is a mathematical and/or algorithmic representation of a relationship between inputs and outputs, as generated using any machine-learning process including without limitation any process as described above, and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include inputs as described in this disclosure as inputs, outputs as described in this disclosure as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 2, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 204.

Referring again to FIG. 1, computing device 104 may be configured to provide plurality of nutritional needs 108 by receiving, from a user, at least a biological extraction, training, using a plurality of nutritional training elements, each nutritional training element including a biological extraction datum and a correlated nutritional recommendation datum, a first machine learning process 112, and generating, using the at least a biological extraction and the first machine learning process 112, the plurality of nutritional needs 108 of the user. Detecting a correlation of at least an element of biological extraction data to at least a nutritional need, for instance and without limitation using machine-learning process, may include detecting an effect of at least an element of biological extraction on at least a nutritional need. Computing device 104 may select at least an element of biological extraction data to which a correlation may be determined; without limitation, selected at least an element of biological extraction data may be transmitted to user and/or a person, entity, and/or device performing a correlation. Alternatively or additionally, existing data, test, or results, for instance, in a database and/or otherwise available to computing device 104 may be retrieved according to selection of at least an element of biological extraction. Selection of at least an element of biological extraction may be performed according to a score or other quantitative datum indicating a degree of impact and/or effect on nutritional need and/or association therewith; in other words, quantitative datum and/or score may indicate a degree to which a given measurement and/or level of a given biological extraction may be correlative with a degree of efficacy and/or accuracy of a nutritional need. At least an element of biological extraction may be selected where quantitative datum and/or score correlates to a value. Any value, quantitative datum, and/or score may be provided by one or more inputs, which may be received directly from submissions via user interface forms or the like, and/or retrieved from a database recording such submissions. In non-limiting examples, a computing device 104 may be configured to support a user interface form which may include a graphical user interface for data input. Graphical user interface may receive data from a user, for instance, by prompting a user to input data that can be collected and organized by a computing device 104. It will be understood by those skilled in the art, after reviewing the disclosure in its entirety, the various ways data may be input in a computing device 104 by a user. Any value, quantitative datum, and/or score may be acquired, for instance in a non-limiting example, from an online source, database, repository, or any other place where data may be available including without limitation, PubMed, National Institutes of Health (NIH), National Science Foundation (NSF), National Academies of Science, Engineering and Medicine, clinical trials, research journals, periodicals, presentations, seminars, studies, trials, medical devices, experiments, or any other source of biological extraction data. Data may be classified to like users, or subsets of users, and training data could be limited to such subsets using a classifier or other identifying means. User classifier may be used to train a machine learning process and/or a supervised machine learning process. Classifier may distinguish a commonality or relationship among users based on, for instance in non-limiting examples, biological extraction and how it relates to a nutrition need. A machine learning process could be trained on a dataset limited to the subset of biological extraction data and its relationship to a nutrition need.

Figure 3:
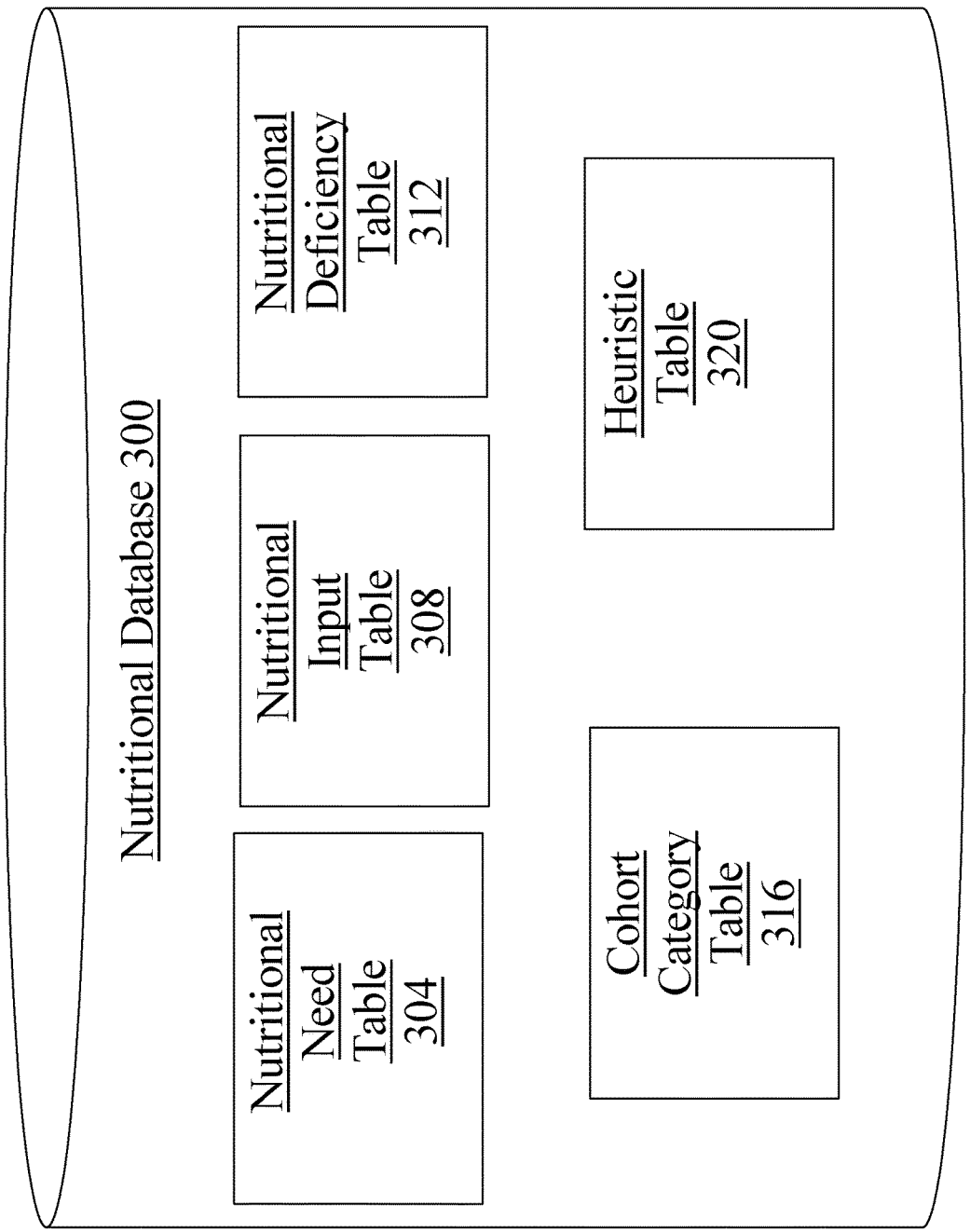
FIG. 3 is a block diagram of an exemplary embodiment of a nutrition database.

Referring now to FIG. 3, a non-limiting exemplary embodiment of a nutrition database 300 is illustrated. Database may be implemented, without limitation, as a relational database, a key-value retrieval database such as a NOSQL database, or any other format or structure for use as a database that a person skilled in the art would recognize as suitable upon review of the entirety of this disclosure. Database may alternatively or additionally be implemented using a distributed data storage protocol and/or data structure, such as a distributed hash table or the like. Database may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

With continued reference to FIG. 3, at least a computing device 104 may, alternatively or additionally, store and/or retrieve data from a nutritional need table 304, nutritional input 116 table 308, and nutritional deficiency 120 table 312. Determinations by a machine learning process may also be stored and/or retrieved from the nutrition database 300, for instance in non-limiting examples a misreporting factor. As a non-limiting example, nutrition database 300 may organize data according to one or more nutrition database 300 tables. One or more database tables may be linked to one another by, for instance in a non-limiting example, common column values. For instance, a common column between two tables of database may include an identifier of a submission, such as a form entry, textual submission, research paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which data from one or more tables may be linked and/or related to data in one or more other tables.

Still referring to FIG. 3, in a non-limiting embodiment, one or more nutritional database tables of a database may include, as a non-limiting example, a nutritional need table 304, which may include nutritional need recommendations for use in predicting nutritional need of a user and/or correlating biological extraction data, entries indicating degrees of relevance to and/or efficacy in predicting nutritional needs 108 of a user, and/or other elements of data computing device 104 and/or system 100 may use to determine usefulness and/or relevance of biological extraction in determining nutritional need as described in this disclosure. One or more tables may include a nutritional need table 304, which may correlate biological extraction data and/or combinations thereof to one or more measures of nutritional need; nutritional need table 304 may contain a plurality of entries associating at least an element of biological extraction data with nutritional need. One or more tables may include, without limitation, a nutritional input 116 table 308 which may contain one or more inputs identifying one or more categories of data, for instance user-reported meals. One or more tables may include, without limitation, a nutritional deficiency 120 table 312, which may contain one or more inputs identifying one or more categories of data, for instance previous user nutrient deficiencies. One or more tables may include, without limitation, a cohort table 316 which may contain one or more inputs identifying one or more categories of data, for instance demographic data, medical history data, physiological data, or the like, with regard to which users having matching or similar data may be expected to have similar nutritional needs 108 and/or nutritional deficiencies as a result of nutritional input 116 elements and/or other biological extraction data. One or more tables may include, without limitation, a heuristic table 320, which may include one or more inputs describing potential mathematical relationships between at least an element of biological extraction data and nutritional needs 108, as described in further detail below. Still referring to FIG. 1, computing device 104 may be configured to determine a nutritional input 116 from a user. As used in this disclosure, a "nutritional input 116" is a nutritional intake of a user as it relates to any of the categories or values represented by a nutritional need, as described previously. Nutritional input 116 refers to at least a value of a nutrient of a plurality of values of nutrients, determined as described herein, which describe an amount of a nutrient from user-reported nutritional intake data. Computing device 104 may determine nutritional input 116 for user by inferring nutritional input 116, using a machine-learning process, from the at least a biological extraction. In a non-limiting example, nutritional input 116 may be determined by at least a computing device 104 from, for instance, user-reported data, user-reported data and a value determined from a database, user-reported data and at least an element of biological extraction, or any combination thereof. As used in this disclosure, "user-reported data" is any nutritional input 116 information, for instance and without limitation, a meal consumed, provided to a computing device 104 from a user. In non-limiting examples, a computing device 104 may receive user-reported data and/or biological extraction data via a graphical user interface, as previously described. A machine-learning process may infer the nutritional input 116s from user-reported data, for instance in non-limiting examples, from user-reported meals mapped to nutrient amounts. Machine learning process may be able to retrieve information from a nutrition database 300, or other source, to determine nutrient values for a user-reported meal to determine the nutritional input 116 of the user. In non-limiting examples, a machine learning process may take nutritional values, for instance as determined in the previously described ways, as an input and use at least a biological extraction to determine the nutritional input 116 for the user, for instance, by taking into account a metabolic disorder or digestive difficulty.

Continuing in referring to FIG. 1, a system 100 determining a nutritional input 116 for the user includes receiving user-reported data describing the nutritional input 116. A computing device 104 may be configured to determine a nutritional input 116 from at least a user-reported datum of a plurality of user-reported data describing nutritional input 116. User-reported nutritional intake data may be, for instance without limitation, meals or food items mapped to nutrition inputs. Mapping user-reported nutritional intake may be performed by a machine learning process or may be mapped using database entries, as described before. Alternatively or additionally, mapping user-reported nutritional intake may be performed by a machine learning model trained with data described herein. Mapping user-reported nutritional intake to determine a nutritional input 116 may, for instance and without limitation, include determining an amount of a vitamin that was consumed from a user-reported meal.

Continuing in referring to FIG. 1, alternatively or additionally, a computing device 104 configured to calculate a user misreporting factor and weighting the user-reported data with the misreporting factor. A "user misreporting factor," as used herein, is a numerical quantity representing a probability or degree of likelihood that a user is over or under-reporting a user-reported nutritional input 116. A machine learning process, such as without limitation a supervised machine learning process may be implemented, as described above, to calculate a user misreporting factor. User misreporting factor can be used to weight user-reported data to generate a nutrition input. A machine learning algorithm may be trained with data retrieved from an available source, for instance from a nutrition database 300 as described herein, including for instance in non-limiting examples data on user nutrient absorption, nutrient pharmacokinetics, digestive disorders, accuracy of nutrition labels, portion sizes, or any data as it relates to the reporting of nutrient intake. In non-limiting examples, a machine learning model may be trained with this data to detect for instance any mathematical, correlational, or other relationship between user nutrition intake and reporting of user nutrition intake, any tendency to underestimate and/or overestimate nutritional intake. A machine learning model may be trained in this manner to calculate at least a user misreporting factor of a plurality of misreporting factors. A machine learning process may use a model trained in the above described manner and user-reported nutrition intake as inputs to calculate a misreporting factor-weighed nutrition input as a generated output. In non-limiting illustrative embodiments, a machine learning model trained for at least a user misreporting factor, may weight, adjust, correct, or otherwise modify user-reported data as it relates to nutritional input 116 to result in more accurate nutritional intake reporting than user-reported data alone.

With continued reference to FIG. 1, computing device 104 is configured to determine a nutritional input 116 to a user, wherein determining the nutritional input 116 to the user comprises receiving user-reported data describing a nutritional input 116, calculating a user misreporting factor, and weighting the user-reported data with the user misreporting factor. This may be performed utilizing any of the methodologies as described herein. Computing device 104 is configured to determine a nutritional input 116 by generating a first machine-learning model, wherein the first machine-learning model utilizes a biological extraction as an input and outputs a nutritional input 116. First machine-learning model may be implemented as any machine-learning model as described herein. First machine-learning model is trained using training data including a plurality of biological extractions and a plurality of correlated nutritional input 116s.

Continuing in referring to FIG. 1, calculating a misreporting factor further comprises using a machine learning process, wherein the machine learning process is trained using training data including a plurality of past user inputs and a plurality of correlated nutritional measurements. A plurality of past user inputs, as described herein may include any user-reported data regarding nutritional intake, for instance in non-limiting examples, a food item or meal. A machine learning process may be trained as previously described may generate a machine learning model with correlated nutritional measurements, as described herein, between past user-reported nutritional input 116s and the current user-reporting. In non-limiting examples machine learning process data, including for instance any models and/or outputs generated from user-reported data, misreporting factors, and/or nutritional input 116s may be stored in a database for training subsequent machine learning models, as illustrated in FIG. 2. A machine learning process may be a supervised learning process, as described herein.

Continuing in referring to FIG. 1, a system 100 determining a nutritional input 116 for the user includes determining a long-term nutritional input 116 pattern. As used herein, "long-term nutritional input 116 pattern" is an element of data describing a consistent rate of consumption and/or a regular quantity consumed, of a nutrient; a long-term nutritional input 116 pattern may include, without limitation, user-reported nutritional input 116 data from days, weeks, months, years, or any amount of time. A machine learning process may determine a long-term nutritional input 116 pattern using a machine learning model trained with at least a correlated nutritional measurement and at least a past user-reported input of a plurality of past user-reported nutritional input 116 to determine a long-term nutritional input 116 pattern. A long-term nutritional input 116 pattern and any associated data may be stored and/or retrieved from a database for use by further machine learning processes. In non-limiting illustrative examples, a machine learning process may extract months of user-reported nutritional intake data from a database to generate a long-term nutritional input 116 pattern. In non-limiting illustrative examples, a long-term nutritional input 116 pattern may include months of user-reported nutritional intake data weighed with a misreporting factor calculated from months of user-reported nutritional intake.

Continuing in reference to FIG. 1, a system 100 determining a nutritional input 116 for a user includes determining a current nutritional input 116. As described in this disclosure, a "current nutritional input 116," is a nutritional input 116 generated from a most recent user-reported nutritional intake or set of intakes, including for instance in non-limiting examples, over a recent period of time such as a day, week, or the like. Alternatively or additionally, a machine learning process and/or model may use any correlated nutritional measurements or other available information, such as a misreporting factor, to generate a current nutritional input 116. In non-limiting examples, a machine learning process may retrieve prior machine learning models and/or outputs, for instance from a nutrition database 300, to generate a current nutritional input 116. In non-limiting embodiments, a machine learning model may be trained with at least an element of biological extraction and/or a long-term nutritional input 116 pattern to generate a model that weights, corrects, or otherwise adjusts user-reported current notational input data. Models trained in this way, as described above, may determine correlated nutritional measurements such as nutrition values, misreporting factors, or any other data related to the calculation of a current nutritional input 116 to weight, adjust, correct, or otherwise modify user-reported nutritional intake data, such as a meal recently consumed. This may include, for instance and without limitation user-reported nutritional input 116 as it is being input into a system 100 in real-time. A machine learning model may be trained, as described above, with at least a first element of biological extraction data and/or at least a most recent user-reported nutrition intake input to determine any correlated nutritional measurements or other relationships in the data. In non-limiting examples, a machine learning process may use a model trained in such a manner and a most recent user-reported input to output a current nutritional input 116.

Continuing in reference to FIG. 1, computing device 104 is configured to detect a nutrition deficiency. As used in this disclosure, a "nutritional deficiency 120," is a calculated value that corresponds to any deficit in a nutrient value between a nutritional need and a nutritional input 116. As a non-limiting example, detecting a nutrition deficiency may include calculating the deficiency using a second machine learning process 124, that inputs the at least a nutritional input 116 and outputs a nutritional deficiency 120. A computing device 104 may be configured to support second machine learning process 124 which may use a nutritional input 116, as described before, as an input to calculate a nutritional deficiency 120 of a user, for instance in non-limiting examples, by calculating a difference between a nutritional input 116 and a nutritional need generating an output value of a plurality of output values. Alternatively or additionally, a second machine learning process 124 may use a nutritional deficiency model 128 trained, as described above, with at least an element of biological extraction data and/or user-reported data to calculate a nutritional deficiency 120. Second machine learning process 124 may include supervised machine learning process. Second machine learning process 124 may calculate a nutrient deficiency using a nutrient input and data retrieved and/or stored on a nutrition database 300. In non-limiting examples, a nutritional deficiency 120 may be calculated by subtracting a nutritional input 116 of a nutrient from a nutritional need of the same nutrient to determine if a deficiency exists.

Continuing in reference to FIG. 1, a system 100 detecting a nutrition deficiency of a user includes detecting a chronic deficiency. A computing device 104 may be configured to detect a chronic deficiency by using a machine learning process, as described before. A machine learning process may be a supervised machine learning process. A "chronic deficiency," as used in this disclosure, is a nutritional deficiency 120 that is present over a long period, or as a persistent pattern. A chronic deficiency may be detected using a long-term nutritional input 116 pattern of a plurality of long-term nutritional input 116 patterns and/or long-term user-reported nutritional intake that indicate a nutritional deficiency 120 is not due to a current nutritional intake deficiency. In non-limiting examples, at least an element of biological extraction may be an input used by a machine learning process to detect a chronic deficiency, for example, blood glucose data as it relates to carbohydrate intake.

Continuing in reference to FIG. 1, a system 100 detecting a nutrition deficiency of a user include detecting an acute deficiency. A computing device 104 may be configured to detect an acute deficiency by using a machine learning process, as described before. A machine learning process may be a supervised machine learning process. An "acute deficiency," as described herein refers to a nutritional deficiency 120 that is present in current user-reported nutrition input, or as a current pattern. An acute deficiency may be detected using a current nutritional input 116 of a plurality of current nutritional input 116s and/or most recent user-reported nutritional intake that indicate a nutritional deficiency 120 is not due to a long-term nutritional intake deficiency and/or long-term nutritional input 116 pattern. In non-limiting examples, at least an element of biological extraction may be an input used by a machine learning process to detect a chronic deficiency, for example, diabetes as it relates to per-meal carbohydrate intake. A machine learning process may determine the difference between a chronic and acute nutritional deficiency 120 and may adjust a supplement dose 132 based on this information.

Alternatively or additionally, and still referring to FIG. 1, detecting nutrition deficiency may include receiving input value training data including a plurality of elements, wherein each element includes at least a nutritional input 116 and a correlated nutritional quantity. [i.e., what are you getting, with regard to each quantity, in your input?]. Computing device 104 may train a second machine-learning process as a function of the input value training data. Computing device 104 may determine a plurality of input quantities as a function of the nutritional input 116. Computing device 104 may then calculate nutritional deficiency 120 as a function of nutritional need and plurality of input quantities, for instance by subtracting the plurality of input quantities from a plurality of corresponding nutritional needs 108.

As a further non-limiting example, and continuing to refer to FIG. 1, computing device 104 may determine nutritional deficiency 120 at least in part directly from biological extraction data. receiving deficiency training data including a plurality of elements, wherein each element includes a biological extraction datum and a correlated nutritional deficiency 120 datum. Computing device 104 may train a nutritional deficiency 120 model as a function of the deficiency training data. Computing device 104 may receive a biological extraction as described above and detecting the nutritional deficiency 120 as a function of the nutritional deficiency 120 model and the biological extraction. This process may be used, without limitation, to determine a chronic deficiency, for which determination from biomarkers may be a more effective technique than extrapolating long-term trends from user-input nutritional input 116s.

Continuing in referring to FIG. 1, computing device 104 is configured to calculate a supplement dose 132 includes a plurality of supplements combined to address a plurality of nutrient deficiencies. A computing device 104 configured to support a machine learning process may calculate at least a supplement dose 132 of a plurality of supplements from the plurality of nutritional needs 108 and at least a nutritional deficiency 120 of a plurality of nutritional deficiencies. A machine learning process may be a supervised machine learning process, as described above. A "supplement dose 132," as used in this disclosure, is an amount of a supplement intended to address a deficiency. In non-limiting examples, a supplement dose 132 may be a calculated value mapped to a nutrient deficiency, wherein without limitation, a supplement value may be a mass amount of a supplement that address a nutrient deficiency by making up the difference required to reach a nutritional need. A machine learning process may use a nutritional need of a plurality of nutritional needs 108, determined as described before, and/or at least a nutritional deficiency 120, calculated as described before, as inputs to generate an output of at least a supplement dose 132 of a plurality of supplements. A machine learning process may use a model trained with at least an element of biological data to generate a supplement dose 132 of a plurality of supplements to address a plurality of nutrient deficiencies. In non-limiting examples, outputs of supplement dose 132s of the plurality of supplements may be stored and/or retrieved from a nutritional database as training data for further machine learning processes. In non-limiting examples, a machine learning process may train a model with prior supplement dose 132 outputs of a plurality of supplements to calculate subsequent supplement dose 132s.

Continuing in referring for FIG. 1, computing device 104 may be configured to generate a nutrient supplementation plan; generation may include calculating at least a supplement dose 132 from the plurality of nutritional needs 108 and at the least a nutrition deficiency. Supplementation plan may be calculated by a computing device 104 configured to support a machine learning process. A machine learning process may be a supervised machine learning process. A supplement plan may comprise a supplement regimen, wherein a supplement regimen may refer to a supplement dose 132 and frequency of use of a plurality of supplements. Supplement regimen may be an instantaneous dose, that is calculated as a single measured dosage for a user such as an amount of mass of a vitamin per amount of mass bodyweight, or a supplement regimen may be a calculated dosage that deviates from this instantaneous dose, for instance in non-limiting examples an amount of mass of a vitamin per amount of mass bodyweight that is taken daily over the span of a month, decreasing in amount each week. Supplement regimen may be any combination of at least an instantaneous dose and at least a second dose of one or more supplements. Supplement plan may include an output of a calculated value of an amount of a supplement and how it addresses at least a nutritional deficiency 120 and/or nutritional need. In non-limiting examples, supplement plan may be determined by a machine learning process that calculates a supplement plan based on input data, for instance, biological extraction data, user-reported data, nutritional need data, nutritional input 116 data, nutritional deficiency 120 data, or any other available data to provide an output corresponding to at least a compatible supplement, a supplement dosage, a user supplement frequency, information on combining a plurality of supplements, and/or how a supplement addresses a deficiency. A machine learning process for calculating, or otherwise adjusting, supplement plan outputs may make use of an algorithm or model trained with data described above. Supplement plan may be determined based on data that corresponds to supplement plan outputs of other users or subsets of users that match user classifiers or other identifiers. Supplement plan outputs may be stored and/or retrieved from a nutritional database to train machine learning models, as described above.

Continuing in reference to FIG. 1, determining a supplement plan may include performing a machine learning process, with user-reported data after a first supplement plan has been recommended as an input, to determine how a user responds to a supplement dosage over time. A computing device 104 and/or machine learning process may use an input that is user-reported data and/or biological extraction data after a supplement plan has been adopted by a user to identify how a user responds to a supplement plan. Machine learning process may be trained, as previously described, with data that corresponds to how a user responds to a supplement plan. Machine learning process trained in this way may be used to inform subsequent supplement plans. These outputs and/or machine learning algorithms and/or models generated from training a machine learning process in this way may represent data that can be used to identify classifiers, or subsets of users, based on how a user responds to a supplement plan. Outputs generated in this manner may be stored and/or retrieved from a database, as described above.

With further reference to FIG. 1, computing device 104 may be configured to select an ingredient combination as a function of the at least a supplement dose 132. In a non-limiting example, selection may include receiving a plurality of ingredients 136 stored at an additive manufacturing device 140. An "additive manufacturing device," as used in this disclosure, is a device that performs additive manufacturing processes. As used in this disclosure, an "additive manufacturing process" is a process in which material is added incrementally to a body of material in a series of two or more successive steps. A material may be added in the form of a stack of incremental layers; each layer may represent a cross-section of an object to be formed upon completion of an additive manufacturing process. Each cross-section may, as a non-limiting example be modeled on a computing device 104 as a cross-section of graphical representation of the object to be formed; for instance, a computer aided design (CAD) tool may be used to receive or generate a three-dimensional model of an object to be formed, and a computerized process, such as a "slicer" or similar process, may derive from that model a series of cross-sectional layers that, when deposited during an additive manufacturing process, together will form the object. Steps performed by an additive manufacturing system to deposit each layer may be guided by a computer aided manufacturing (CAM) tool. Persons skilled in the art will be aware of many alternative tools and/or modeling processes that may be used to prepare a design for additive manufacture, including without limitation the production of stereolithography (STL) files and the like. In an embodiment, a series of layers are deposited in a substantially radial form, for instance by adding a succession of coatings to the workpiece. Similarly, a material may be added in volumetric increments other than layers, such as by depositing physical voxels in rectilinear form or other forms. Deposition of material in an additive manufacturing process may be accomplished by any suitable means, including without limitation any "three-dimensional printing" process. Additive manufacturing processes may include fused deposition modeling processes, material that may be melted, such as chocolate, caramel, gelatin, or the like is deposited in a molten or otherwise fluid form in successive layers, each of which is cured by natural cooling or other means. Additive manufacturing processes may include processes that deposit successive layers of powder and binder; the powder may include any edible flour, including cereal rice, or other flours, any powdered foodstuff, sugar, salt, or the like. Powder may include one or more powdered supplements. Binder may include any edible adhesive material, any material that may be deposited in liquid and/or semi-liquid form as described above with regard to fused deposition, or the like. Additive manufacturing may include depositing and sintering materials having melting points such as chocolate, cheese or the like where sintering may be accomplished using selective laser sintering and/or other processes of alternatively heating and cooling to adhere layers together, by applying fluid or paste-like materials such as doughs in strips or sheets and then curing that material either by cooling, heating and/or cooking, or the like.

Figure 4:
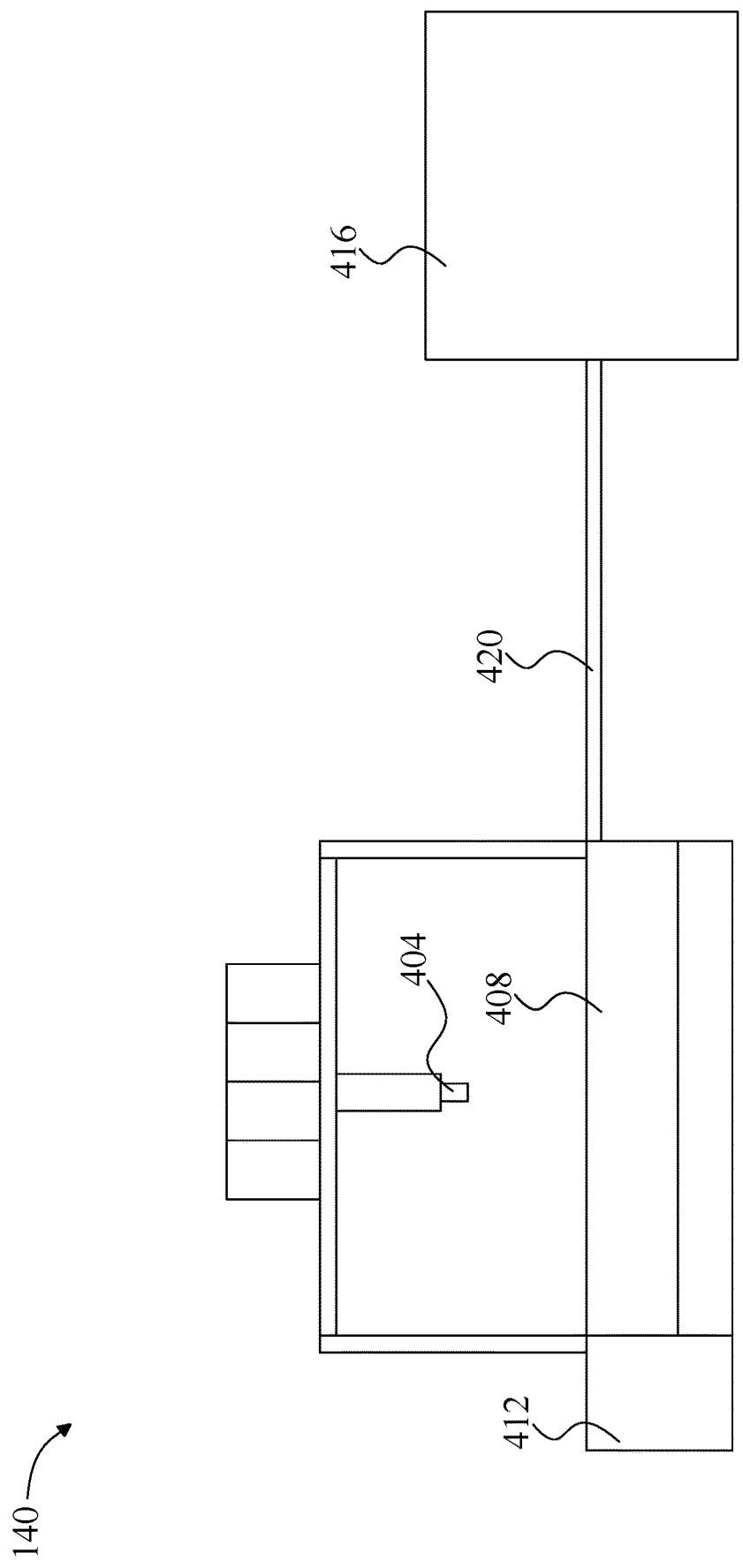
FIG. 4 is a schematic diagram of an exemplary embodiment of an additive manufacturing device.

Referring now to FIG. 4, a block diagram of an exemplary embodiment of a additive manufacturing device 140 is illustrated. Additive manufacturing device 140 may include at least an applicator 404. At least an applicator 404 may include any device used to deposit layers of food. For instance, applicator 404 may include a printer head for a 3D printer. Applicator 404 may include an extruding device for extruding fluid or paste material, a sprayer or other applicator for bonding material, an applicator for powering, a sintering device such as a laser, or other such material. Applicator 404 may draw upon one or more reservoirs of liquid, paste, and/or powdered materials, which may advance such materials to application using, without limitation, auger screws, pistons, gravity, and/or pressure.

Continuing to view FIG. 4 additive manufacturing device 140 may include a workpiece support 408. Workpiece support 408 may be a structure that supports a workpiece during the one or more manufacturing steps. Workpiece support 408 may include a base table. Base table may include a surface to which a workpiece or other components may be secured. Surface may be oriented horizontally, vertically, or in any other orientation. Surface may be substantially planar. Workpiece support 408 may include a substrate for initial deposition of material in an additive process.

Additive manufacturing device 140 may include a powered additive manufacturing device 140. As used herein, a powered additive manufacturing device 140 is a additive manufacturing device 140 in which at least one component of the additive manufacturing device 140 includes at least a component powered by something other than human power. At least a component may be powered by any non-human source, including without limitation electric power generated or stored by any means, heat engines including steam, internal combustion, or diesel engines, wind power, water power, pneumatic power, or hydraulic power. Powered components may include any components of additive manufacturing device 140. Applicator 404 may be powered; for instance, applicator 404 may include an endmill mounted on a spindle rotated by a motor (not shown). Workpiece support 408 may be powered. Where additive manufacturing device 140 is a mechanical device, motion of components along linear or rotary constraints may be powered; for instance, motion of base table along one or more linear constraints such as linear slides may be driven by a motor or other source of power. Similarly, rotation of rotary table may be driven by a power source. Tool-changer, where present, may be driven by power. In some embodiments, all or substantially all of the components of additive manufacturing device 140 are powered by something other than human power; for instance, all components may be powered by electrical power.

Additive manufacturing device 140 may include an automated manufacturing system. In some embodiments, an automated manufacturing system is a additive manufacturing device 140 including a controller 412 that controls one or more manufacturing steps automatically. Controller 412 may include a sequential control device that produces a sequence of commands without feedback from other components of automated manufacturing system. Controller 412 may include a feedback control device that produces commands triggered or modified by feedback from other components. Controller 412 may perform both sequential and feedback control. In some embodiments, controller 412 includes a mechanical device. In other embodiments, controller 412 includes an electronic device. Electronic device may include digital or analog electronic components, including without limitation one or more logic circuits, such one or more logic gates, programmable elements such as field-programmable arrays, multiplexors, one or more operational amplifiers, one or more diodes, one or more transistors, one or more comparators, and one or more integrators. Electronic device may include a processor. Electronic device may include a computing device 104. Computing device 104 may include any computing device 104 as described below in reference to FIG. 5. Computing device 104 may include a computing device 104 embedded in additive manufacturing device 140; as a non-limiting example, computing device 104 may include a microcontroller 412, which may be housed in a unit that combines the other components of additive manufacturing device 140. Controller 412 may include a manufacturer client of plurality of manufacturer clients; controller 412 may be communicatively coupled to a manufacturer client of plurality of manufacturer clients.

Controller 412 may include a component embedded in additive manufacturing device 140; as a non-limiting example, controller 412 may include a microcontroller 412, which may be housed in a unit that combines the other components of additive manufacturing device 140. Further continuing the example, microcontroller 412 may have program memory, which may enable microcontroller 412 to load a program that directs additive manufacturing device 140 to perform an automated manufacturing process. Similarly, controller 412 may include any other components of a computing device 104 as described below in reference to FIG. 5 in a device housed within additive manufacturing device 140. In other embodiments, controller 412 includes a computing device 104 that is separate from the rest of the components of additive manufacturing device 140; for instance, controller 412 may include a personal computer, laptop, or workstation connected to the remainder of additive manufacturing device 140 by a wired or wireless data connection. In some embodiments, controller 412 includes both a personal computing device 104 where a user may enter instructions to generate a program for turning workpiece into a finished product, and an embedded device that receives the program from the personal computing device 104 and executes the program. Persons skilled in the art will be aware of various ways that a controller 412, which may include one or more computing device, may be connected to or incorporated in an automated manufacturing system as described above.

Controller 412 may control components of automated manufacturing system; for instance, controller 412 may control elements including without limitation tool changer to switch endmills, spindle or gear systems operatively coupled to spindle to regulate spindle rotational speed, linear movement of applicator 404, base table, or both, and rotation or rotational position of rotary table. As an example, applicator 404 may be moved about using computerized numerical control (CNC) devices and/or motion controls that are automated and operate by precisely programmed commands that control movement of one or more parts of the equipment to effect the material removal. CNC machines, their operation, programming, and relation to computer aided manufacturing (CAM) tools and computer aided design (CAD) tools are well known and need not be described in detail herein for those skilled in the art to understand the scope of the present invention and how to practice it in any of its widely varying forms. Similarly, controller 412 may coordinate deposition and/or curing of material in additive manufacturing processes, where additive manufacturing device 140 is an additive manufacturing device 140. Persons skilled in the art, upon reading the entirety of this disclosure, will be aware of similar automated control systems usable for various forms manufacturing. Controller may be, be included in, include, and/or be in communication with computing device 104.

Still referring to FIG. 4, additive manufacturing device 140 may include an oven 416 or other heat source in which and/or with which a partially or wholly completed food product may be cooked, baked, heated, or the like; alternatively or additionally, a laser or other heat source at applicator may apply heat to food products in process of manufacture. One or more conveyors 420 may transfer food products between support structure and oven 416 or other components.

In operation, additive manufacturing device 140 may deposit layers of edible material, including without limitation powdered supplements and/or substrates, as programmed by computing device 104 and/or controller 412; such programming may be driven, in turn, by selected ingredient lists as described in further detail below.

Still referring to FIG. 4, computing device 104 may receive a plurality of ingredients 136, where receiving in this context refers to receiving data describing the plurality of ingredients 136. Plurality of ingredients 136 may include one or more supplements in powered form; applicator and/or other components of additive manufacturing device 140 may be controllable to administer and/or apply precise quantities of each powdered supplement, such that exactly an amount needed, as determined above, is applied and no more. Plurality of ingredients 136 may include at least a substrate ingredient, where a "substrate ingredient" is an ingredient that acts as a binder and/or as a layer of material on which and/or into which powdered supplement material may be placed. Plurality of ingredients 136 may include one or more flavor ingredients 136, where "flavor ingredients 136" are defined for the purposes of this disclosure as ingredients 136 that are used to produce one or more flavors, for instance as specified by a user; one or more flavors ingredients 136 may include spices, sweeteners, salt, acids such as citric acid, sources of bitterness, and/or sources of umami. In an embodiment, a user may request one or more flavors and/or flavor profiles, which may be programmed into computing device 104 and/or controller 412; in other words, computing device 104 may receive a user flavor preference and select ingredient combination as a function of the user flavor preference. For instance, and without limitation, computing device 104 and/or controller 412 may be programmed to produce one or more preconfigured recipes, such as a chocolate bar recipe having chocolate ingredients 136 and/or flavors, a caramel bar recipe having caramel deposited thereon, or the like. User may alternatively or additionally enter an instruction specifying a desired texture; in other words, computing device 104 may receive a user texture preference and select the ingredient combination as a function of the user texture preference. For instance, user may request a chewy or soft texture, and computing device 104 and/or controller 412 may use a gelatinous material combined with flour or the like to create a soft or chewy texture, while a request for a crunchy texture may result in inclusion of crunchy substrate materials and/or baking and/or toasting the serving at one or more stages of deposition to produce a crunchy texture. Users may request both flavors and textures simultaneously, resulting, for instance, in a chewy chocolate-flavored bar, a crunchy cinnamon-flavored bar, or the like. Still referring to FIG. 1, computing device 104 is configured to initiate manufacture of a nutritional supplement serving at the additive manufacturing device. Initiation of manufacture may include performance of a first step in the removal from or deposition of material to create part; first step may include a particular milling or cutting operation, such as the performance of a registration cut, a first deposition of material in a fused deposition modeling process, or the like. First step may include location of a workpiece at an additive manufacturing device; location may include placement in a precise position and/or registration within a coordinate system used by additive manufacturing device to guide particular manufacturing steps. First step may include generation of a control instruction initiating manufacturing steps; generation of a control instruction may include transmission of a signal to initiate manufacture and/or transmission of any machine control instruction sets generated as described above, including without limitation transmission of information for localized and machine-specific machine-control instruction generation. Transmission may be direct or indirect; for instance, transmission may involve transmission to a remote device that relays transmission to an additive manufacturing device or computing device 104 coupled thereto, or transmission to an auxiliary computing device 104 or computer memory for transport to the additive manufacturing device and/or computing device 104 coupled thereto. System may produce toolpaths for use by automated device; such toolpaths may instruct a device to produce all or a portion of the part.

Figure 5:
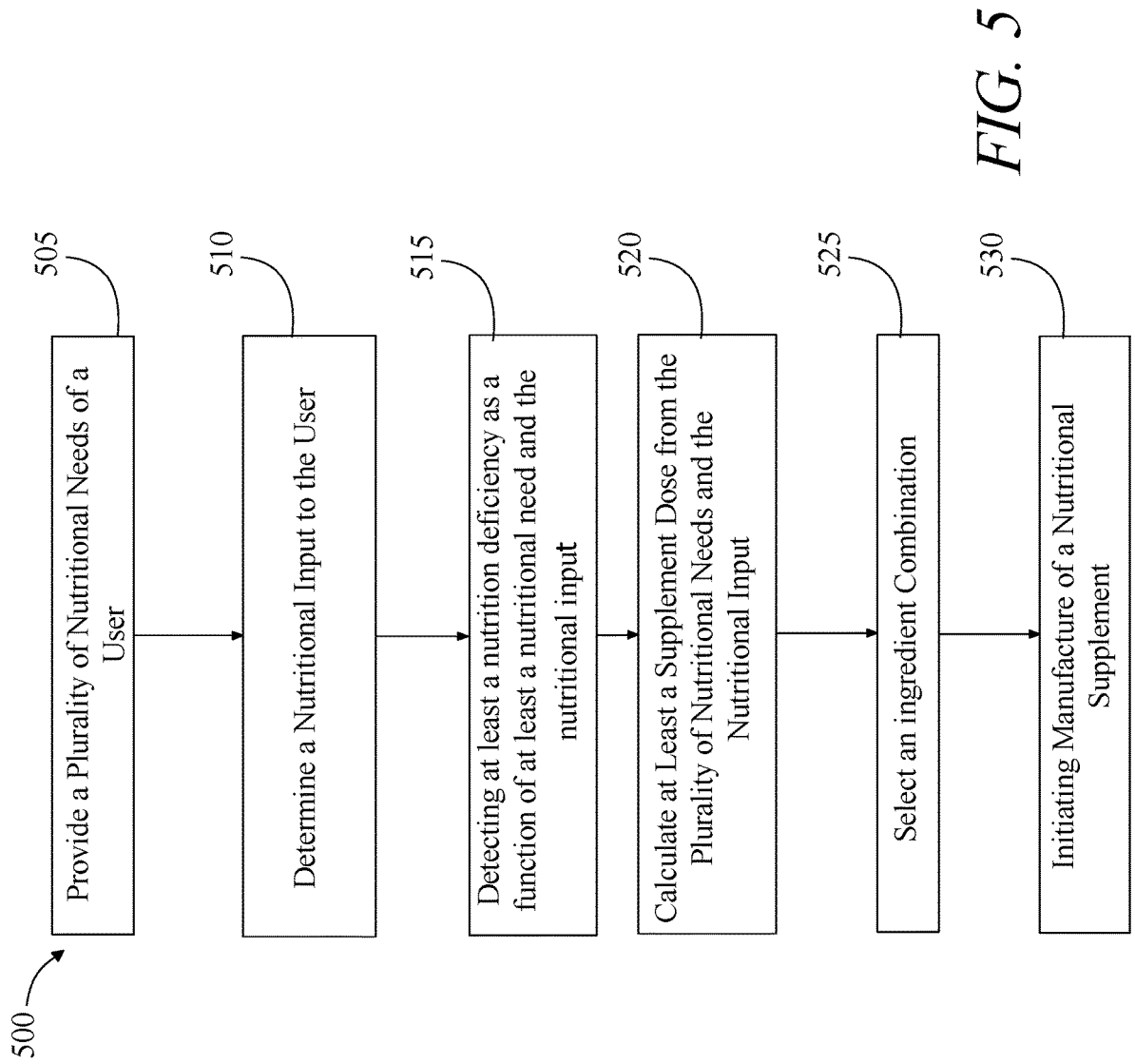
FIG. 5 is a flow diagram of an exemplary embodiment of a method of additive manufacturing of nutritional supplement servings.

Referring now to FIG. 5, an exemplary embodiment of a method 500 of additive manufacturing of nutritional supplement servings is illustrated. At step 505, a plurality of nutritional needs 108 of a user are provided at a computing device 104; this may be implemented, without limitation, as described above in reference to FIGS. 1-4. providing the plurality of nutritional needs 108 may include receiving, from a user, at least a biological extraction, training, using a plurality of nutritional training elements, each nutritional training element including a biological extraction datum and a correlated nutritional recommendation datum, a first machine learning process 112, and generating, using the at least a biological extraction and the first machine learning process 112, the plurality of nutritional needs 108 of the user.

At step 510, and still referring to FIG. 5, computing device 104 determines a nutritional input 116 to the user; this may be implemented, without limitation, as described above in reference to FIGS. 1-4. Receiving nutritional input 116 may include receiving a long-term nutritional input 116 pattern. Receiving nutritional input 116 may include receiving a current nutritional input 116.

At step 515, and continuing to refer to FIG. 5, computing device 104 detects at least a nutrition deficiency as a function of the plurality of nutritional needs 108 and the nutritional input 116; this may be implemented, without limitation, as described above in reference to FIGS. 1-4. Detecting nutrition deficiency may include receiving input value training data including a plurality of elements, wherein each element includes at least a nutritional input 116 and a correlated nutritional quantity, training a second machine-learning process as a function of the input value training data, determining a plurality of input quantities as a function of the nutritional input 116, and calculating the nutritional deficiency 120 as a function of the nutritional need and the plurality of input quantities. Detecting nutritional deficiency 120 may include receiving deficiency training data including a plurality of elements, wherein each element includes a biological extraction datum and a correlated nutritional deficiency 120 datum, training a nutritional deficiency 120 model as a function of the deficiency training data, receiving a biological extraction associated with the user, and detecting the nutritional deficiency 120 as a function of the nutritional deficiency 120 model and the biological extraction. Detecting nutrition deficiency may include detecting a chronic deficiency. Detecting a nutrition deficiency may include detecting an acute deficiency.

At step 520, and still referring to FIG. 5, computing device 104 calculates at least a supplement dose 132 from the plurality of nutritional needs 108 and at the least a nutrition deficiency; this may be implemented, without limitation, as described above in reference to FIGS. 1-4.

At step 525, and further referring to FIG. 5 computing device 104 selects an ingredient combination as a function of the at least a supplement dose 132, wherein selecting further comprises; this may be implemented, without limitation, as described above in reference to FIGS. 1-4. As a non-limiting example, this may be accomplished by receiving a plurality of ingredients 136 stored at an additive manufacturing device, wherein the plurality ingredients 136 includes a plurality of supplement ingredients 136 and at least a substrate ingredient and selecting an ingredient combination including at least a substrate ingredient and at least a supplement ingredient as a function of the nutritional deficiency 120. Computing device 104 may receive a user flavor preference and select ingredient combination as a function of the user flavor preference. Computing device 104 may receiving a user texture preference and select ingredient combination as a function of the user texture preference. At step 530, computing device 104 initiates manufacture of a nutritional supplement serving at the additive manufacturing device; this may be implemented, without limitation, as described above in reference to FIGS. 1-4.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 6:
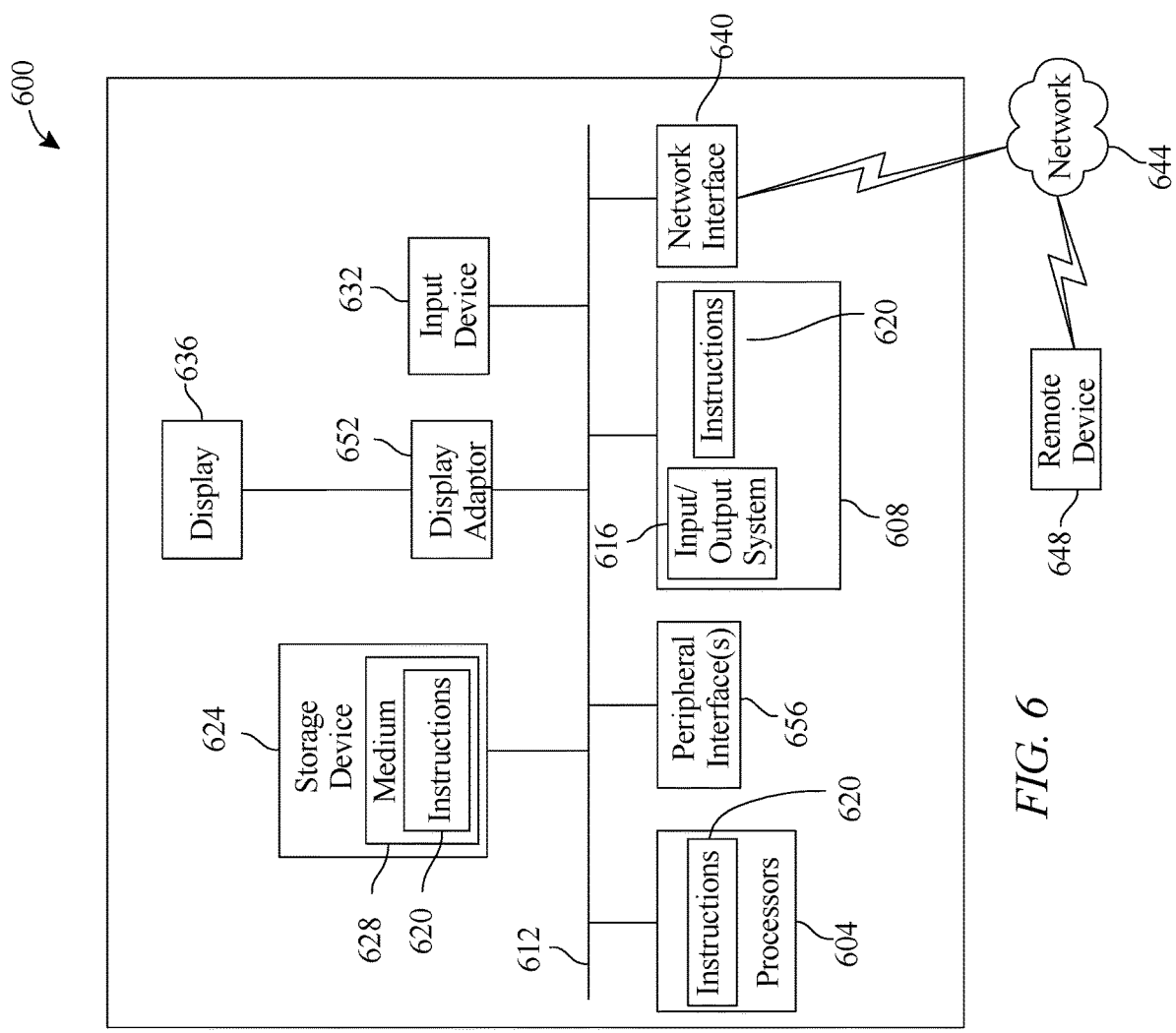
FIG. 6 is a block diagram of a computing system that can be used to implement any one or more of the methodologies disclosed herein and any one or more portions thereof.

FIG. 6 shows a diagrammatic representation of one embodiment of a computing device in the exemplary form of a computer system 600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Processor 604 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 604 may be organized according to Von Neumann and/or Harvard architecture as a non-limiting example. Processor 604 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 608 may include various components (e.g., machine-readable media) including, but not limited to, a random-access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Computer system 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Computer system 600 may also include an input device 632. In one example, a user of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIREWIRE interface, a direct interface to bus 612, and any combinations thereof. Input device 632 may include a touch screen interface that may be a part of or separate from display 636, discussed further below. Input device 632 may be utilized as a user selection device for selecting one or more graphical representations in a graphical interface as described above.

A user may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote devices 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Computer system 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for additive manufacturing of nutritional supplement servings, the system comprising a computing device, wherein the computing device comprises a processor, the processor is designed and configured to:
    receive a nutritional need of a user;
    receive a user texture preference;
    determine a nutritional input of the user;
    determine a user misreporting factor, wherein the user misreporting factor is a numerical quantity representing a degree of likelihood that a user is under-reporting a user-reported nutritional input, wherein determining the user misreporting factor comprises determining the user misreporting factor based on accuracy of past user-reported nutritional inputs retrieved from a database, wherein the user misreporting factor is used to weigh user-reported data to generate a nutrition input, and wherein the user misreporting factor modifies the user-reported data as it relates to the nutritional input;
    adjust the nutritional input of the user as a function of the user misreporting factor;
    detect a deficit between the nutritional need of the user and the nutritional input of the user;
    calculate a supplement dose as a function of the nutritional need of the user and the deficit, wherein the supplement dose is an amount of a supplement intended to address a nutritional deficiency, wherein the nutritional deficiency comprises a chronic deficiency and an acute deficiency, and wherein calculating the supplement dose further comprises:
        detecting a chronic deficiency using a first supervised machine learning process, wherein the chronic deficiency is detected using a long-term nutritional input pattern of a plurality of long-term nutritional input patterns to indicate a nutritional deficiency;
        detecting an acute deficiency using a second supervised machine learning process, wherein the acute deficiency is detected using a current nutritional input and a user-reported nutritional intake that indicate a nutritional deficiency;
        determining the deficit as a function of a difference between the input quantity and the nutritional need of the user and the difference between the chronic deficiency and the acute nutritional deficiency; and
        determining the supplement dose mapped to the deficit;
    generate a nutrient supplementation plan, wherein generation of the nutrient supplementation plan includes calculating the supplement dose from the nutritional need and the nutritional deficiency, wherein the nutrient supplementation plan comprises a supplement regimen, wherein the supplement regimen refers to the supplement dose and frequency of use of the supplement;
    select an ingredient combination as a function of the supplement dose and the user texture preference, wherein selecting the ingredient combination further comprises:
        receiving a plurality of ingredients stored at an additive manufacturing device, said additive manufacturing device comprising an applicator configured to deposit at least a portion of the ingredient combination, and wherein the plurality of ingredients include a plurality of supplement ingredients and at least a substrate ingredient; and
        selecting the ingredient combination including the at least a substrate ingredient and the at least a supplement ingredient as a function of the supplement dose and the user texture; and
    initiate the applicator to deposit successive layers, wherein the successive layers include a portion of the at least a substrate ingredient and the at least a supplement ingredient, wherein depositing the successive layers comprises sintering the successive layers together using a laser.

2. The system of claim 1, wherein the computing device is configured to receive the plurality of nutritional needs by:
    receiving, from a user, at least a biological extraction;
    training, using a plurality of nutritional training elements, each nutritional training element including a biological extraction datum and a correlated nutritional recommendation datum, a first machine learning process; and
    generating, using the at least a biological extraction and the first machine learning process, the plurality of nutritional needs of the user.

3. The system of claim 1, wherein determining the nutritional input of the user further comprises receiving a long-term nutritional input pattern.

4. The system of claim 1, wherein determining the nutritional input of the user further comprises receiving a current nutritional input.

5. The system of claim 1, wherein detecting the deficit further comprises:
    receiving deficiency training data including a plurality of elements, wherein each element includes a biological extraction datum and a correlated nutritional deficiency datum;
    training a nutritional deficiency model as a function of the deficiency training data;
    receiving a biological extraction associated with the user; and
    detecting the deficit as a function of the nutritional deficiency model and the biological extraction.

6. The system of claim 1, wherein the computing device is further configured to:
receive a user flavor preference; and
select the ingredient combination as a function of the user flavor preference.

7. The system of claim 1, where adjusting the nutritional input of the user comprises weighing the nutritional input with the user misreporting factor.

8. The system of claim 1, wherein determining the user misreporting factor comprises receiving training data correlating nutritional intake to user misreporting factors.

9. A method of additive manufacturing of nutritional supplement servings, the method comprising:
receiving, by a processor, a nutritional need of a user;
receiving, by the processor, a user texture preference;
determining, by the processor, a nutritional input of the user;
determining, by the processor, a user misreporting factor, wherein the user misrepresenting factor is a numerical quantity representing a degree of likelihood that a user is under-reporting a user-reported nutritional input, wherein determining the user misreporting factor comprises determining the user misreporting factor based on accuracy of past user-reported nutritional inputs retrieved from a database, wherein the user misreporting factor is used to weigh user-reported data to generate a nutrition input, and wherein the user misreporting factor modifies the user-reported data as it relates to the nutritional input;
adjusting, by the processor, the nutritional input as a function of the user misreporting factor;
detecting, by the processor, a deficit between the nutritional need of the user and the nutritional input of the user;
calculating, by the processor, a supplement dose as a function of the nutritional need of the user and the deficit, wherein the supplement dose is an amount of a supplement intended to address a nutritional deficiency, wherein the nutritional deficiency comprises a chronic deficiency and an acute deficiency and wherein calculating the supplement dose further comprises:
detecting a chronic deficiency using a first supervised machine learning process, wherein the chronic deficiency is detected using a long-term nutritional input pattern of a plurality of long-term nutritional input patterns to indicate a nutritional deficiency;
detecting an acute deficiency using a second supervised machine learning process, wherein the acute deficiency is detected using a current nutritional input and a user-reported nutritional intake that indicate a nutritional deficiency;
determining the deficit as a function of a difference between the input quantity and the nutritional need of the user and the difference between the chronic deficiency and the acute deficiency; and
determining the supplement dose mapped to the deficit;
generating, by the processor, a nutrient supplementation plan, wherein generation of the nutrient supplementation plan includes calculating the supplement dose from the nutritional need and the nutritional deficiency, wherein the nutrient supplementation plan comprises a supplement regimen, wherein the supplement regimen refers to the supplement dose and frequency of use of the supplement;

selecting, by the processor, an ingredient combination as a function of the supplement dose and the user texture preference, wherein selecting the ingredient combination further comprises:
receiving a plurality of ingredients stored at an additive manufacturing device, said additive manufacturing device comprising an applicator configured to deposit at least a portion of the ingredient combination, and wherein the plurality of ingredients include a plurality of supplement ingredients and at least a substrate ingredient; and
selecting the ingredient combination including the at least a substrate ingredient and the at least a supplement ingredient as a function of the supplement dose and the user texture preference; and
initiating, by the processor, the applicator to deposit successive layers, wherein the successive layers include a portion of the at least a substrate ingredient and the at least a supplement ingredient, wherein depositing the successive layers comprises sintering the successive layers together using a laser.

10. The method of claim 9, receiving the plurality of nutritional needs further comprises:
receiving, from a user, at least a biological extraction;
training, using a plurality of nutritional training elements, each nutritional training element including a biological extraction datum and a correlated nutritional recommendation datum, a first machine learning process; and
generating, using the at least a biological extraction and the first machine learning process, the plurality of nutritional needs of the user.

11. The method of claim 9, wherein determining the nutritional input further comprises receiving a nutritional input pattern.

12. The method of claim 9, wherein determining the nutritional input further comprises receiving a current nutritional input.

13. The method of claim 9, wherein detecting the deficit further comprises:
receiving deficiency training data including a plurality of elements, wherein each element includes a biological extraction datum and a correlated nutritional deficiency datum;
training a nutritional deficiency model as a function of the deficiency training data;
receiving a biological extraction associated with the user; and
detecting the deficit nutritional deficiency as a function of the nutritional deficiency model and the biological extraction.

14. The method of claim 9 further comprising:
receiving a user flavor preference; and
selecting the ingredient combination as a function of the user flavor preference.

15. The method of claim 9, where adjusting the nutritional input of the user comprises weighing the nutritional input with the user misreporting factor.

16. The method of claim 9, wherein determining the user misreporting factor comprises:
receiving training data correlating nutritional intake to user misreporting factors;
training a machine-learning process as a function of the training data; and determining the user misreporting factor as a function of the machine-learning process, wherein the machine-learning process inputs user-reported nutrition intake and outputs the user misreporting factor.

\* \* \* \* \*